United States Patent
Yarussi et al.

(10) Patent No.: US 6,181,427 B1
(45) Date of Patent: Jan. 30, 2001

(54) COMPACT OPTICAL REFLECTOMETER SYSTEM

(75) Inventors: Richard A. Yarussi, Mountain View; Blaine R. Spady, San Jose, both of CA (US)

(73) Assignee: Nanometrics Incorporated, Sunnyvale, CA (US)

(*) Notice: Under 35 U.S.C. 154(b), the term of this patent shall be extended for 0 days.

(21) Appl. No.: 09/347,362

(22) Filed: Jul. 6, 1999

Related U.S. Application Data (60) Provisional application No. 60/092,384, filed on Jul. 10, 1998.

(51) Int. Cl.[7] .................................................. G01N 21/55
(52) U.S. Cl. ........................................... 356/445; 356/328
(58) Field of Search ................................... 356/445, 446, 356/447, 448, 346, 328; 250/339.08, 339.11, 372; 359/224

(56) References Cited

U.S. PATENT DOCUMENTS

| | | | |
|---|---|---|---|
| Re. 34,783 | 11/1994 | Coates | 250/372 |
| 3,572,951 | * 3/1971 | Rothwarf . | |
| 4,368,983 | * 1/1983 | Bennett | 356/445 |
| 4,552,458 | * 11/1985 | Lowne | 356/446 |
| 5,024,493 | 6/1991 | Fantozzi et al. | 350/1.3 |
| 5,517,312 | 5/1996 | Finarov | 356/386 |
| 5,747,813 | 5/1998 | Norton et al. | 250/372 |
| 6,061,129 | * 5/2000 | Ershov et al. | 356/328 |

* cited by examiner

Primary Examiner—Hoa Q. Pham
(74) Attorney, Agent, or Firm—Downs Rachlin & Martin PLLC (57) ABSTRACT

A highly compact reflectometer system (10) for obtaining reflectance data and images from a sample (18). The reflectometer includes a light source (20) for generating a beam (Bi), a beam splitter (44) for transmitting a portion of the beam toward the sample, a lens (52) for focusing the transmitted light onto the sample, a video camera (104) for viewing a field of view (56) created by the light focused on the sample, and a spectrometer (86) for detecting and analyzing the spectrum of the light reflected from the sample. The reflectometer preferably includes a number of fold mirrors (FM1–FM6) which make the reflectometer highly compact.

18 Claims, 10 Drawing Sheets

COMPACT OPTICAL REFLECTOMETER SYSTEM

This application claims priority from U.S. Provisional Patent Application Serial No. 60/092,384, filed on Jul. 10, 1998.

FIELD OF THE INVENTION

The present invention relates to reflectometers, and in particular to a highly compact optical reflectometer system for obtaining reflectance data and images from a sample.

BACKGROUND OF THE INVENTION

There is much demand in industry for compact measurement systems and techniques for measuring the reflectance of devices, such as computer chips, flat panel displays, magnetic media used in data storage, and the like, during their manufacturing.

In many optical applications, there is often a need for designs having a high degree of compactness. For example, U.S. Pat. No. 5,024,493 to Fantuzzi et al. discloses a highly compact folded infra-red optical system having an effective focal length of about 240 mm and which employs three fold mirrors to fit the system into a package having a diameter of approximately 150 mm. Such compactness of design is technically challenging, but can result in significant advantages. In the present case, it enables accurate, spectroscopic, reflectance measurements of a sample where such sophisticated equipment could not previously be implemented due to space limitations. Such compactness can also result in cost-savings where space is at a premium.

Present day metrology instruments, including those using reflectometer systems, tend to be large and physically separated from the processing tools used to fabricate the devices. These processing tools are often in clean rooms, where air quality, temperature and humidity are tightly controlled. Conventional metrology instruments require 1.4–2.0 square meters of this costly clean room floor space. In addition, these metrology instruments are physically separated from the processing tools, so samples have to be removed from the processing tools and transferred to the metrology instruments. Often the environment inside the processing tool is designed to be even cleaner than the surrounding area. In such a case, the wafer must be placed in a sealed, airtight container while it is transferred. This takes time, causing costly delays in the production line.

Therefore, it is advantageous to integrate these metrology instruments into the processing tool. However, these processing tools are already designed to be as compact as possible because of the above mentioned cost of the clean room facilities in which they are housed. Thus, the size of an integrated metrology instrument is the determining factor in its ability to be integrated into a processing tool. At the same time, an integrated metrology instrument must provide highly accurate measurements of the samples in order to provide useful information on the performance of the processing tool. In addition, an integrated metrology instrument must provide these measurements quickly so as not to slow the production line.

SUMMARY OF THE INVENTION

The present invention is a compact, high performance optical reflectometer. It has been designed with the above-mentioned size, accuracy, and speed requirements in mind. The reflectometer may be mounted anywhere space is at a premium, and may be easily integrated into various types of manufacturing apparatus, such as semiconductor processing tools.

A first aspect of the invention is a compact reflectometer system capable of measuring reflectance from a sample. The reflectometer comprises illumination, signal and viewing subsystems. The illumination subsystem is for illuminating the sample and includes a light source, and at least one illumination subsystem fold mirror. The illumination subsystem forms a light beam, which illuminates a field of view (FOV) on the sample. The signal subsystem is for measuring at least one wavelength of light from the light source reflected from the sample and includes at least one signal subsystem fold mirror. The signal subsystem detects light reflected from a small, well-defined measurement spot in the center of the FOV. The viewing subsystem is for viewing the sample and includes at least one viewing subsystem fold mirror and captures a video image of the FOV. This image is used to locate areas of interest on the sample, so that the measurement spot may be precisely positioned within it. The reflectometer is designed such that the illuminating, signal and viewing subsystems occupy a volume of less than or equal to approximately 0.006 cubic meters.

The reflectometer of the present invention is designed to be highly compact. Many of the optical elements serve more than one purpose, thereby minimizing the total number of optical elements. The design also accounts for multiple fold mirror mounting planes for mounting multiple fold mirrors, with certain subsystems sharing certain fold mirrors. This allows the entire reflectometer to occupy a very small (i.e., 0.006 cubic meters) volume, even though the optical path for all the subsystems combined is about 0.9 meters.

By placing the reflectometer on an (x,y) or (r, theta) stage, it can be moved relative to a sample in order to measure different points on the sample. Conversely, the sample may be moved while the reflectometer is held fixed. The reflectometer may be used as the core of a tabletop system. It may be mounted onto a vacuum chamber, where it may measure a sample contained in the vacuum chamber through a viewport on the chamber. Because the system has no moving optical elements it is stable, reliable and mechanically simple

DETAILED DESCRIPTION OF THE INVENTION

The present invention relates to reflectometers, and in particular to a highly compact optical reflectometer system for obtaining reflectance data and images from a sample. The reflectometer system of the present invention is modular and sufficiently compact to be easily integrated into various types of manufacturing apparatus, such as semiconductor processing tools.

First, the layout and operation of the reflectometer of the present invention is described with reference to a partially folded version, for the sake of simplicity. Then, the design considerations involved in laying out the partially folded reflectometer so that it can be completely folded and made highly compact using multiple fold mirrors are discussed. Then, the insertion of the fold mirrors into the reflectometer in accordance with the teachings of the present invention to obtain a high degree of compactness is described.

Figure 2:
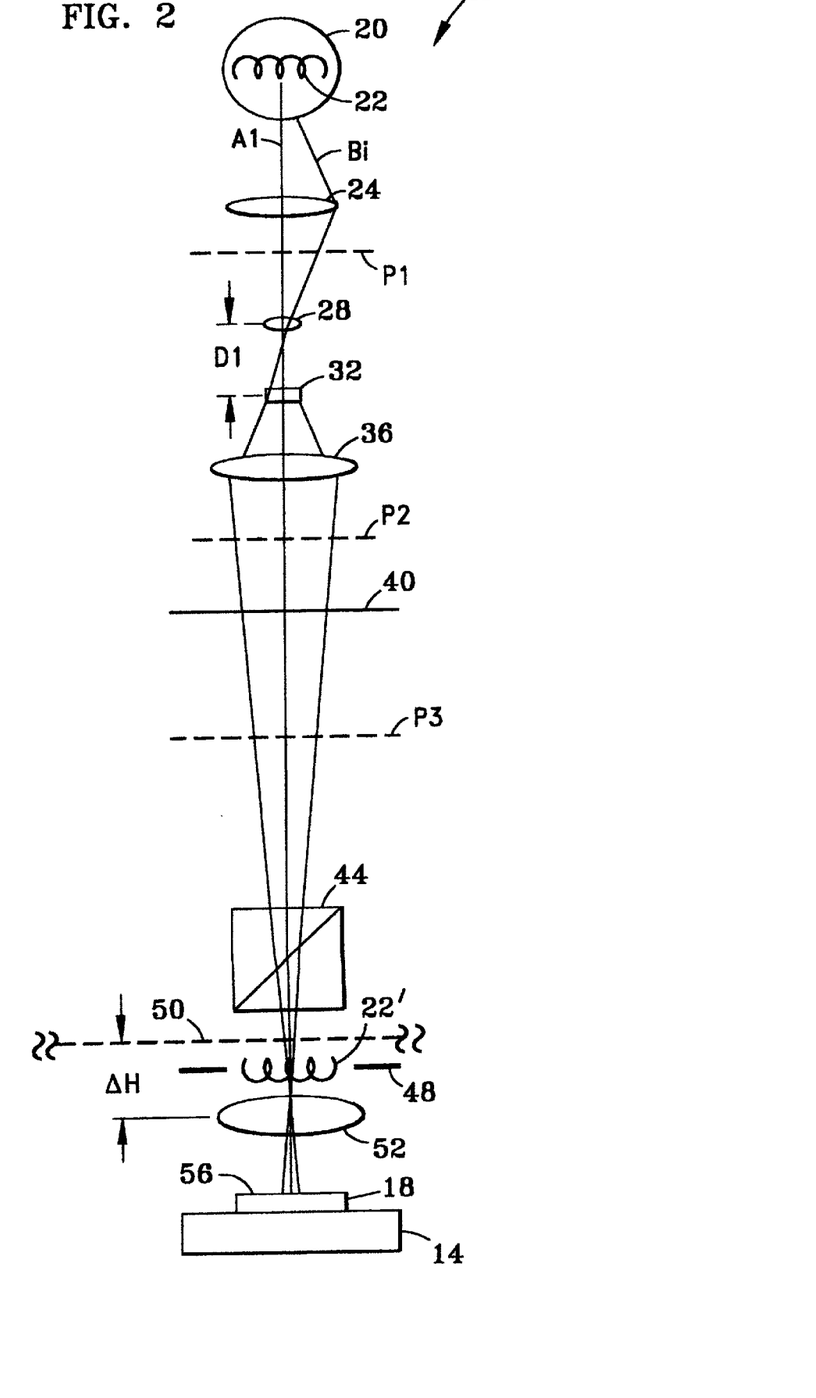
FIG. 2 is an unfolded schematic diagram of the illumination subsystem of the reflectometer system shown in FIG. 1.
Figure 3:
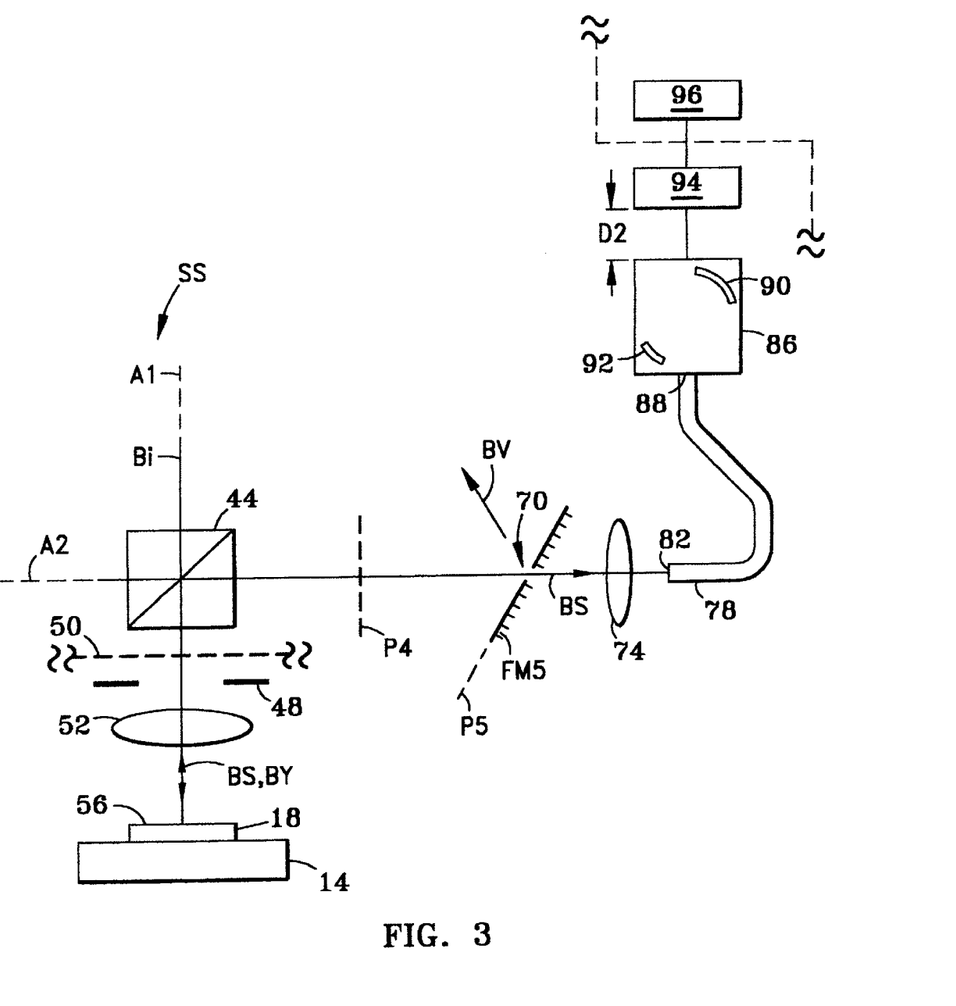
FIG. 3 is a partially folded schematic diagram of the signal subsystem of the reflectometer shown in FIG. 1.
Figure 4:
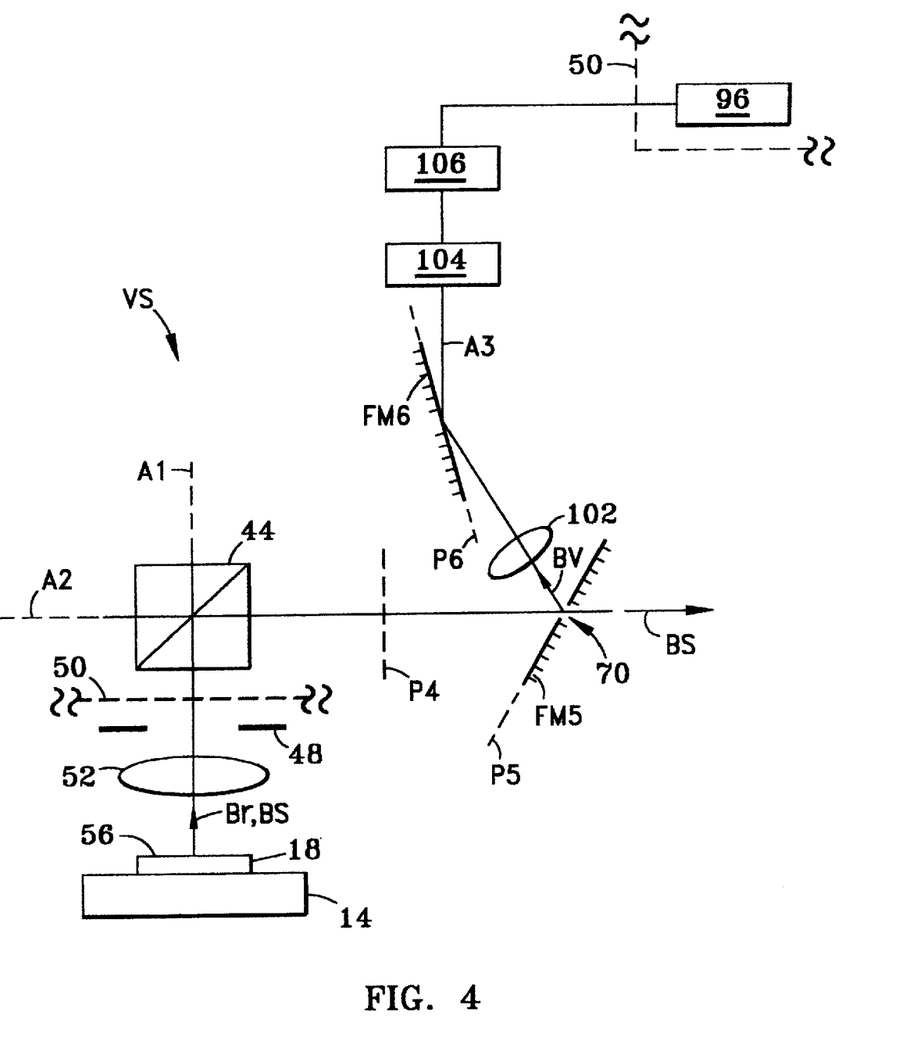
FIG. 4 is a partially folded schematic diagram of the viewing subsystem of the reflectometer shown in FIG. 1.

With reference to FIGS. 1–4, reflectometer 10 (FIG. 1) comprises an illumination subsystem IS along optical axis A1 (FIG. 2), a signal subsystem SS along optical axes A1 and A2 (FIG. 3), and a viewing subsystem VS along axes A1, A2, and A3 (FIG. 4).

Figure 1:
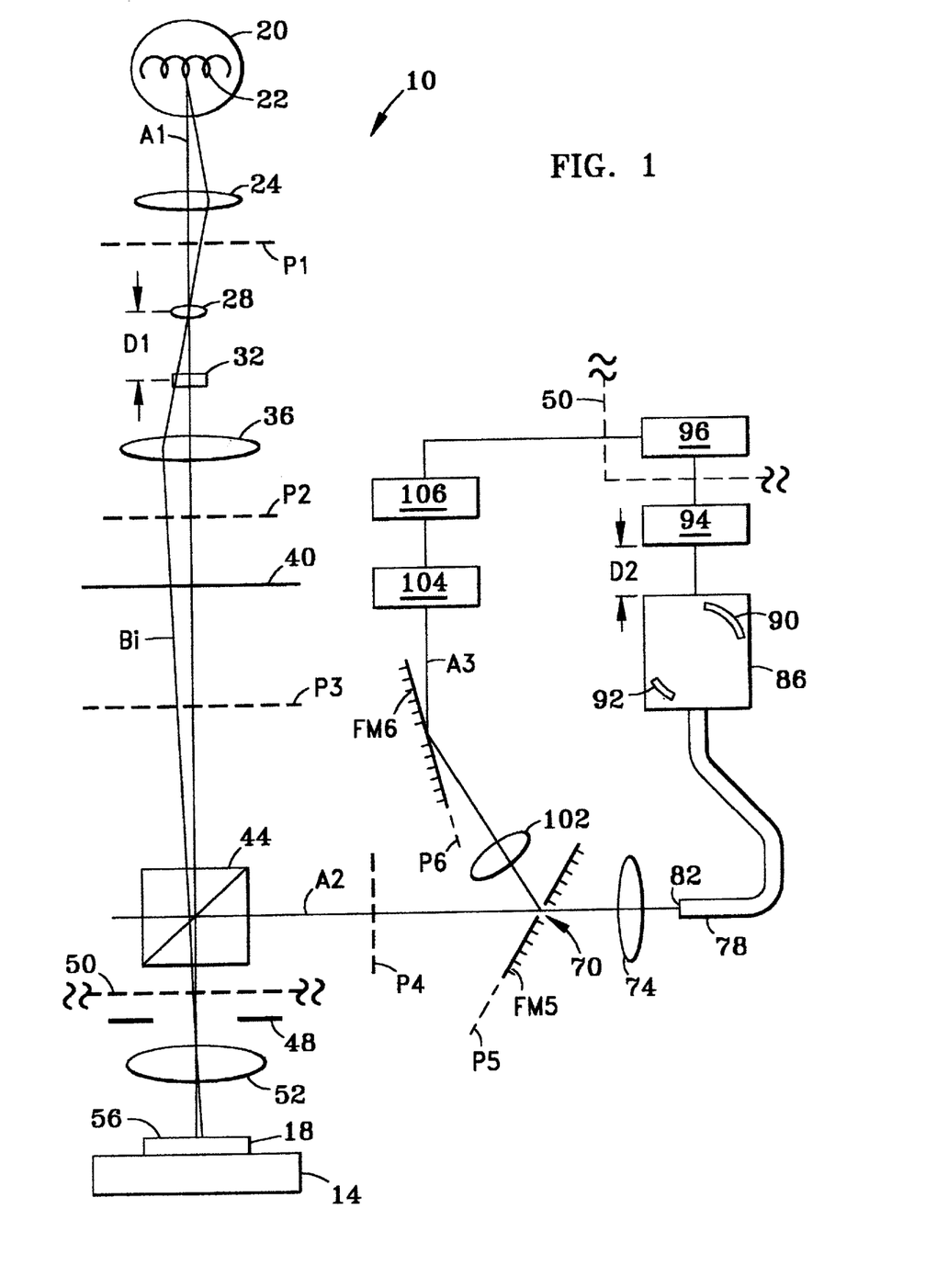
FIG. 1 is a partially folded schematic diagram of the reflectometer system of the present invention, with fold mirror mounting planes shown as dashed lines.

Reflectometer 10 is interfaced with a sample holder 14 for holding a sample 18 whose reflectivity is to be measured.

An important aspect of the present invention is that many of the optical components comprising each reflectometer subsystem are used in more than one subsystem, thereby reducing the number of elements, and making reflectometer 10 amenable to being highly compact. Another related important aspect of reflectometer 10 of the present invention is that the optical path is folded in three-dimensional space using a plurality of fold mirrors placed in accordance with the teachings of the invention, thereby rendering the reflectometer highly compact. This compactness provides reflectometer 10 with many desirable qualities, such as the ability to be take accurate, spectroscopic, reflectance measurements of a sample where such sophisticated equipment could not previously be implemented due to space limitations. Equipment used in semiconductor fabrication facilities is designed to be as compact as possible since the facilities cost hundreds of dollars per square foot to manufacture.

With reference to FIG. 2, illumination subsystem IS of reflectometer 10 is now described. Illumination subsystem IS comprises, in order along optical axis A1, a light source 20 having a filament 22 which emits an illuminating beam Bi which travels along axis A1. Light source 20 may be a monochromatic light source, such as a laser, or a broadband light source, such as a mercury arc lamp. Further, light source 20 may operate at any wavelength or range of wavelengths from the deep ultraviolet to the far infrared.

Adjacent light source 20 is a lens 24. Lens 24, like all lenses in the present invention, may be dioptric, catoptric or catadioptric, and may comprise a single element, or may be a complex multi-element microscope objective, or the like. Adjacent lens 24 is a fold mirror mounting plane P1, for mounting the first of six fold mirrors designed to provide the reflections necessary to achieve a high degree of compactness. The placement of fold mirrors in their respective fold mirror mounting planes is described in more detail, below.

Adjacent fold mirror mounting plane P1 is an aperture stop 28 disposed conjugate with light source 20, a field stop 32, a lens 36, and a second fold mirror mounting plane P2 for mounting the second of six fold mirrors. Adjacent plane P2 is a shutter 40 and a third fold mirror mounting plane P3 for mounting the third of six fold mirrors. Adjacent plane P3 is a beam splitter 44, which may be a cube beam splitter (as shown) or a plate beam splitter. Beam splitter 44 may have a thin-film coating to optimize transmission and reflection of certain wavelengths of light in light beam Bi. Beam splitter 44 may also consist of a double sided mirror mounted at substantially 45 degrees with respect to Bi, and placed such that it reflects some fraction of Bi along optical axis A2 while allowing the remainder of Bi to continue to sample 18. Adjacent beam splitter 44 along optical axis A1 is an aperture stop 48 and a lens 52. Aperture stop 48 is arranged to be conjugate to aperture stop 28 and light source 20.

Also shown in FIG. 2 (as well as in FIGS. 1, 3 and 4) is a housing wall 50 (dashed line). As shown, aperture stop 48 and lens 50 may extend beyond housing wall 50 by a distance ΔH to facilitate placing lens 50 proximate sample 18. Alternatively, aperture stop 48 and lens 50 may be inside housing wall 50.

With continuing reference to FIG. 2, illumination subsystem IS operates as follows. First, filament 22 in light source 20 emits light beam Bi, which travels along axis A1. Light beam Bi travels to lens 24, which images filament 24 onto aperture stop 28. Aperture stop 28 serves to limit the size of the image (not shown) of light source 20 and defines the size of an "effective" light source. Light beam Bi then travels to field stop 32 which is arranged to be conjugate with sample 18, and thus serves to limit the size of light beam Bi imaged onto the sample. Light beam Bi then passes through lens 36, beamsplitter 44, aperture stop 48, and lens 52, thereby illuminating sample 18. Light beam Bi continues through beam splitter 44 along axis A1 and passes through aperture stop 48, where image 22' of filament 22 is formed. Lens 52 then forms an image of field stop 32 onto sample 18, thereby defining a field-of-view (FOV) 56 with light beam Bi. Shutter 40 may be placed anywhere in the illumination subsystem IS.

With reference now to FIG. 3, signal subsystem SS is now described. Signal subsystem comprises in order from sample 18 along axes A1 and A2, lens 52, aperture stop 48, and beamsplitter 44. Signal subsystem SS further includes a fold mirror mounting plane P4 located along axis A2, for inserting the fourth of six fold mirrors. Further included in signal subsystem SS downstream from plane P4 is a fold mirror FM5 mounted in fold mirror mounting plane P5. Fold mirror FM5 has an aperture 70 therein. Adjacent fold mirror FM5 is a lens 74 and a fiber optic 78 having a face 82. Fiber optic 78 is connected to a spectrometer 86 through a spectrometer entrance slit 88. In a preferred embodiment of the present invention, light passing through aperture 70 is focused by lens 74 directly onto entrance slit 88. In another preferred embodiment, aperture 70, fold mirror FM5 and entrance slit 88 are one in the same.

Spectrometer 86 includes a light dispersing element 90, such as a diffraction grating or a prism, and also includes a detector 92, such as a CCD array or photodiode array. Spectrometer 86 is electronically connected to spectrometer electronics 94, which in turn, is electronically connected to a computer 96, which may reside outside of reflectometer 10, as indicated by the dashed line representing housing wall 50. Spectrometer electronics 94 may include, for example, an analog-to-digital (A/D) electronics board. Computer 96 may, for example, comprise a PENTIUM™ microprocessor, and may include pattern recognition (PR) software and/or hardware for identifying the location of objects or structures present on sample 18.

With continuing reference to FIG. 3, the operation of signal subsystem SS is now described. As discussed above, light beam Bi passes through beam splitter 44 and illuminates FOV 56 on sample 18. When light beam Bi is reflected from sample 18, it is now comprised of signal light beam Bs, and viewing light beam Bv. Combined beam Bs+Bv passes back through lens 52 and aperture stop 48, where it is reflected by beam splitter 44 to travel along axis A2 toward fold mirror FM5. At FM5 combined beam Bs+Bv is divided into its constituent beams. Viewing beam Bv is reflected by FM5 into the viewing subsystem VS which will be described below. Signal beam Bs passes through aperture 70 in fold mirror FM5 and is focused by lens 74 onto face 82 of fiber optic 78. The latter then guides light in light beam Bs to entrance slit 88 and into spectrometer 86. The light entering spectrometer 86 is then dispersed into its constituent wavelengths by dispersing element 90, and the wavelength spectrum is detected by detector 92. Detector 92 converts light energy into an electrical signal, which is sent to spectrometer electronics 94 for processing, and then to computer 96 for analysis and, if necessary, storage. This operation provides the sample reflectivity measurements for determining the various optical properties of sample 18, such as thin film thickness and refractive index.

With reference now to FIG. 4, viewing subsystem VS is now described. Viewing subsystem VS comprises, in order from sample 18 along axis A1, axis A2 and axis A3, lens 52, aperture stop 48, beam splitter 44, plane P4, fold mirror FM5 disposed in plane P5, a lens 102, a fold mirror FM6 disposed in fold mirror mounting plane P6, a video camera 104, video camera electronics 106 electronically connected to the video camera, and computer 96 electronically connected to the video electronics. Video camera 104 may be, for example, a CCD camera.

With continuing reference to FIG. 4, the operation of viewing subsystem VS is now described. As discussed above, light beam Bv emanates from sample 18 and is reflected by beam splitter 44 to travel along axis A2 toward fold mirror FM5, which reflects said beam along axis A3 to lens 102. Lens 102 serves to converge light beam Bv. Light beam Bv is then reflected by fold mirror FM6 disposed in plane P6, and is directed onto video camera 104, which records an image (not shown) of FOV 56. The image of FOV 56 contains a black circle (spot) in the center, corresponding to the portion of light beam Bi (i.e., the portion that forms light beam Bs) that passes through aperture 70. Computer 96 then analyzes and, if necessary, stores the video image (or images) of FOV 56 captured by video camera 104. Thus, viewing subsystem VS allows reflectometer 10 to be properly aligned relative to sample 18.

As is well known in the art, before a reflectometer is used it must be referenced. The light energy reflected by a sample with known reflectance is measured using signal subsystem SS. This data, along with the known reflectance of the reference sample, are used to calculate a system response function. Then, the intensity of light measured from a sample with an unknown reflectance can be measured, and combined with the known system response function, the reflectance of the unknown sample can be calculated.

Now, with reference to FIGS. 1–3, the operation of reflectometer 10 is briefly described. First, shutter 40 is closed and the dark current associated with detector 90 is measured. Then, a reference sample is placed on sample holder 14. Shutter 40 is opened, thereby allowing light beam Bi to illuminate the known sample over FOV 56. The light energy reflected from the sample is measured by signal subsystem SS, and a system response function calculated. Then, an unknown sample 18 is placed on sample holder 14, and the light energy is measured by signal subsystem SS. The reflectance of the unknown sample can then calculated as described above.

The precise placement of sample 18 can be established by an operator viewing FOV 56 through viewing subsystem VS and moving sample holder 14 into the proper position. Alternatively, the placement of sample 18 is determined by pattern recognition software analyzing video images obtained via viewing subsystem VS and providing automatic feedback for moving sample holder 14, as described below.

Note that the only moving parts in reflectometer 10 is shutters 40. This simple design contributes to making reflectometer 10 highly compact and extremely reliable.

Figure 5:
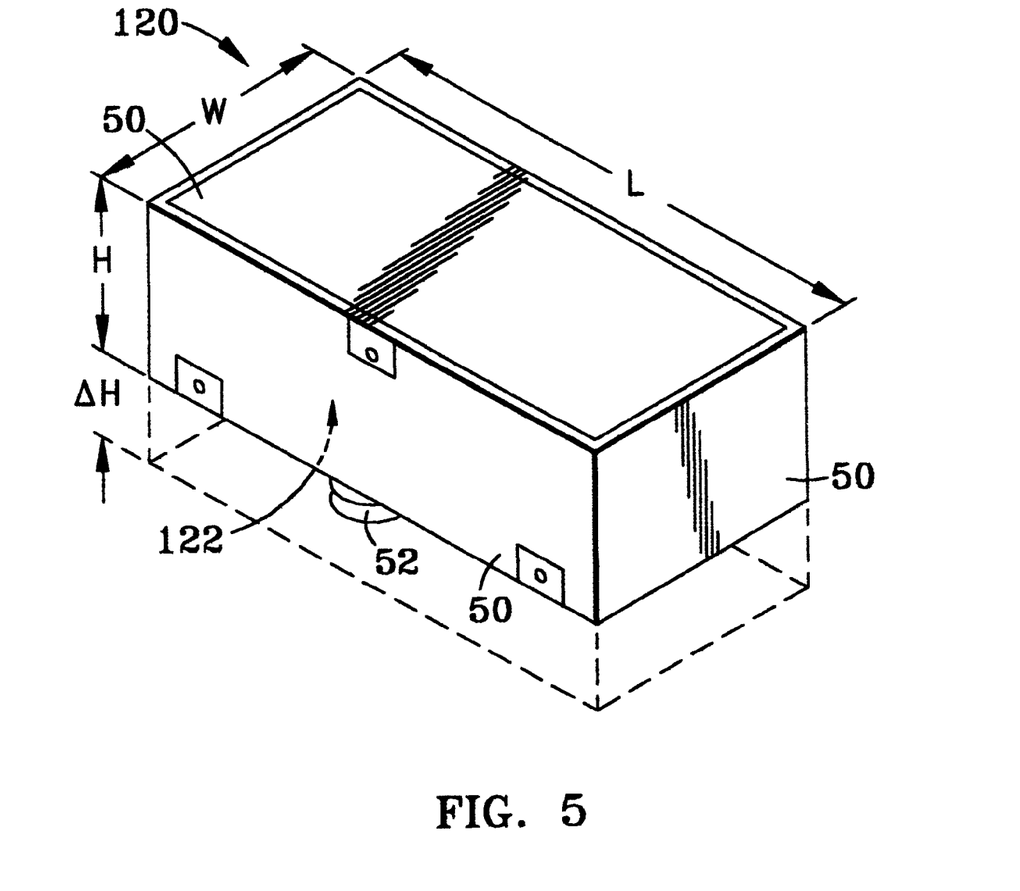
FIG. 5 is a perspective view of a rectangular reflectometer housing of dimensions of approximately 25.4 cm×12.5 cm×10 cm housing the reflectometer of FIG. 1, and having an associated reflectometer volume of about 0.0032 cubic meters.

With reference now to FIG. 5, housing 120 for housing reflectometer 10 includes walls 50, a side 122 and is a rectangular structure having a rectangular volume V (i.e., "housing volume") defined by dimensions L×W×H. Lens 52 and aperture stop 48 preferably extend a distance ΔH (and are contained within a volume ΔV) beyond wall 50 of side 122 to facilitate making measurements of sample 18 (see FIG. 1), as described above. Accordingly, an extended rectangular volume V' is defined by dimensions V+ΔV, which is the rectangular volume occupied by all the elements comprising reflectometer 10 (V' is hereinafter referred to as the "reflectometer volume"). Generally, housing volume V has a value between 0.003 and 0.006 cubic meters, and ΔV has a value between 0 and 5 cubic centimeters. In a preferred embodiment, housing 120 has dimensions of approximately L×W×H=25.4 cm×12.5 cm×10 cm, with ΔV preferably about 1.5 cubic centimeters. Thus, housing 120 encloses a housing volume V of approximately 0.0032 cubic meters. Because of the small value of ΔV, housing 120 has a housing volume V that is substantially the same as the reflectometer volume V'.

For reflectometer 10 to occupy such a highly compact volume, its optical path must be folded in conjunction with certain design considerations, set forth below. In a preferred embodiment, the present invention employs six fold mirrors FM1–FM6 disposed in fold mirror planes P1–P6, as described above. The role of fold mirrors FM1–FM6 in creating a highly compact reflectometer is also discussed below.

Design Considerations

Several design considerations pertinent to achieving the highly compact reflectometer system of the present invention are now described.

With reference again to FIGS. 1 and 2, the first design consideration pertains to the layout of illumination subsystem IS, which is important to both the overall size and function of reflectometer 10. Illumination subsystem IS needs to provide uniform, high-intensity illuminating at sample 18. However, light from light source 20 typically has a highly non-uniform intensity distribution.

As is well known in the art, most microscope illuminators use Kohler illumination. With Kohler illumination in illuminating system IS, light source 20 forms an image (not shown) at aperture stop 48. Lens 52 defocuses this image and directs it to sample 18, which is then uniformly illuminated over FOV 56. Since field stop 32 is conjugate to sample 18, the closer aperture stop 28 is to sample 18, the more in-focus aperture stop 28 will be at the sample. Where light source 20 includes a filament 22, the filament is imaged to aperture stop 28. Accordingly, the structure of filament 22 will be seen at sample 18 if aperture stop 28 and field stop 32 are too close together. Thus, the minimum preferred axial distance D1 between aperture stop 28 and field stop 32 for achieving a suitably uniform illumination of sample 18 over FOV 56 is about 20 mm.

Another design consideration pertaining to illumination subsystem IS that the image of filament 22 must fill aperture stop 48 of lens 52 to maximize the brightness of the illumination. This fixes the magnification $\beta_{IS}$ between aperture stop 28 and aperture stop 48 at about 3.5.

The two above-described constraints combine to fix the focal length $f_{36}$ of lens 36 to be no less than 30 mm. If focal length $f_{36}$ is shorter than 30 mm, a shorter optical path length for illumination subsystem IS results. However, while a shorter optical path is preferable from the point of view of achieving compactness, the illuminating uniformity would suffer, with the consequence that the performance of reflectometer 10 as a whole would suffer.

With reference now to FIGS. 1 and 4, another design consideration pertains to viewing subsystem VS and obtaining an accurate image of FOV 56 with video camera 104. One purpose of video camera 104 is to supply an image to pattern recognition software included in computer 96. The PR software can be taught to look for particular structures on sample 18, thereby allowing reflectometer 10 to make measurements automatically over the sample. This eliminates the need for an operator to first determine the sites at which measurements should be taken and then move sample holder 14 to the proper location. To accomplish making automated measurements, a number of steps need to be carried out. In the first step, sample 18 is disposed within FOV 56. In the second next step, a video image of FOV 56 is obtained by video camera 104. In the third step, a frame of the video image obtained in step 2 is converted to a still image. In the fourth step, the PR software looks for patterns in the image, and a mathematical description of the image is stored. In the fifth step, subsequent video images are analyzed to look for the patterns identified and stored in the fourth step. The pattern or patterns may now be displaced or rotated within FOV 56 by moving sample holder 14 to achieve proper automatic alignment.

Thus, to achieve the above-described automatic alignment, the characteristics of FOV 56 are an important design consideration in making reflectometer 10 highly compact. With continuing reference to FIGS. 1 and 4, since video camera 104 has a fixed number of image elements (pixels), the spatial resolution is determined by FOV 56. If FOV 56 is too small, then larger structures (patterns) on sample 18 cannot easily be viewed or located. Also, a given pattern on sample 18 will contain more pixels, which slows the operation of the PR software. Conversely, if FOV 56 is too large, then the resolution of the viewing subsystem is degraded and patterns on sample 18 cannot be located accurately. It has been found that a FOV 56 of approximately 1.3 mm×1 mm gives good resolution, and is large enough to encompass any object of interest.

A further design consideration for making reflectometer 10 highly compact is minimizing distortion in the image of FOV 56 obtained with viewing subsystem VS. If distortion in viewing subsystem VS causes the viewed image to be different from the taught image in the PR software, then the PR software takes longer to locate the pattern. If the PR software is to locate the pattern quickly and accurately, distortion, which can change the shape of the pattern, must be minimized.

Generally, a maximum distortion of approximately 2% is tolerable in pattern recognition viewing systems. It is well known in the art of optics large fields of view tend to generate distortion. Distortion increases with increased image height h, relative to focal length f. In reflectometer 10, image height h is fixed by the size of the image-recording medium in video camera 104 (e.g., the size of the CCD array). Thus to reduce distortion, one must increase f. However, for a viewing subsystem with magnification m, the length 1 of viewing subsystem VS increases in direct proportion to f. In reflectometer 10 of the present invention, the value of the magnification m from sample 18 to CCD camera 104 is approximately 4.7. Thus, lens 102 having a focal length $f_{102}$ of approximately 40 mm provides the shortest viewing subsystem length which yields acceptable less than 2% distortion.

With reference again to FIG. 1, another design consideration for making reflector 10 highly compact is the distance D2 between spectrometer 86 and spectrometer electronics 94. Analog electrical signals generated by detector 92 from light incident thereon are susceptible to electromagnetic noise while being carried to spectrometer electronics 94. It is thus common practice in the art to keep the distance D2 less than 1 meter under good (i.e., low noise) conditions, and substantially less if there is electromagnetic noise present. In many of the applications for which reflectometer 10 of the present invention is intended, there will be substantial electromagnetic noise present. Accordingly, it is preferable to have the spectrometer electronics 94 within housing 120 (see FIG. 4), and to have the distance D2 as small as possible.

In a preferred embodiment of the present invention, spectrometer electronics 94 comprise an A/D board, which is disposed such that electronic signals from spectrometer 86 only have to travel approximately 3 inches to the spectrometer electronics. Once the data in the electronic signals are digitized by the A/D board, they can be reliably transmitted 10 feet or more to computer 96.

Placement of the Fold Mirrors

Figure 6:
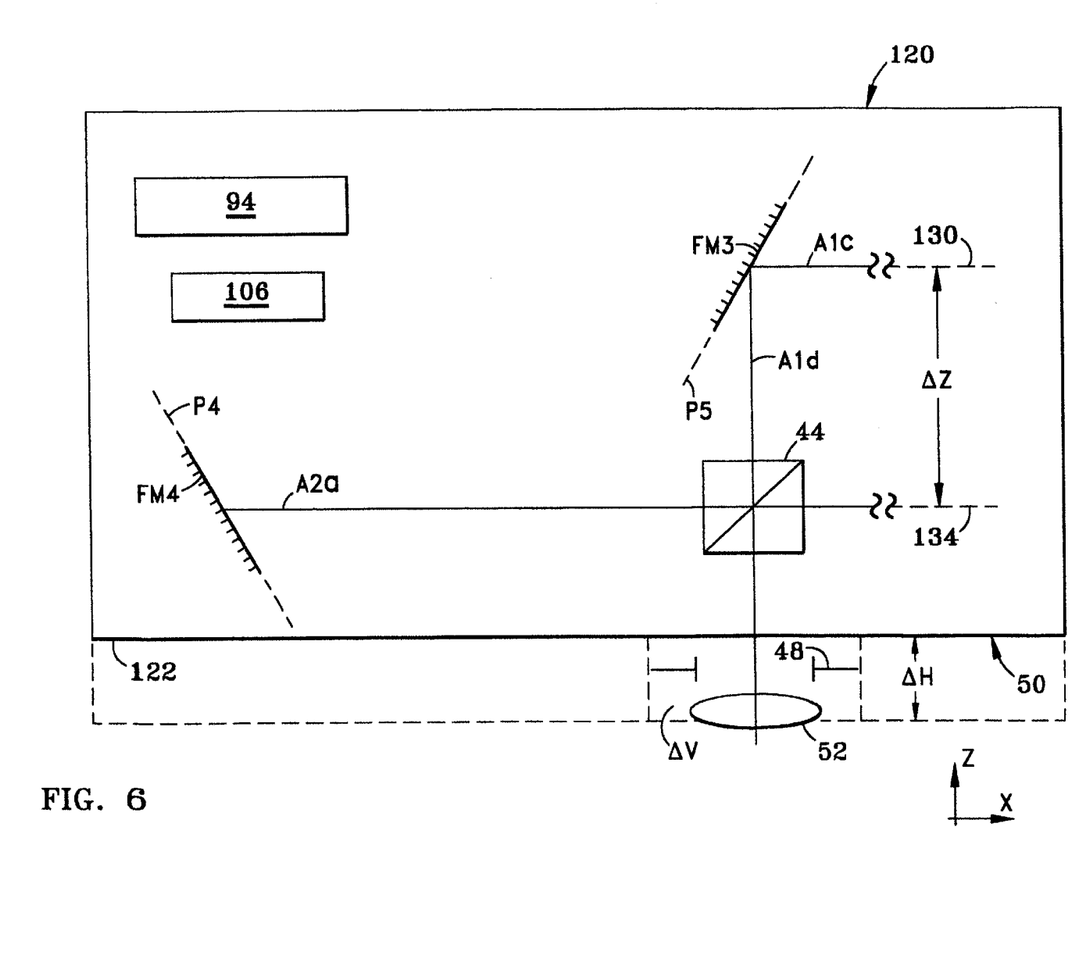
FIG. 6 is a side view of the folded schematic reflectometer system of the present invention as fits within the housing shown in FIG. 5.
Figure 7:
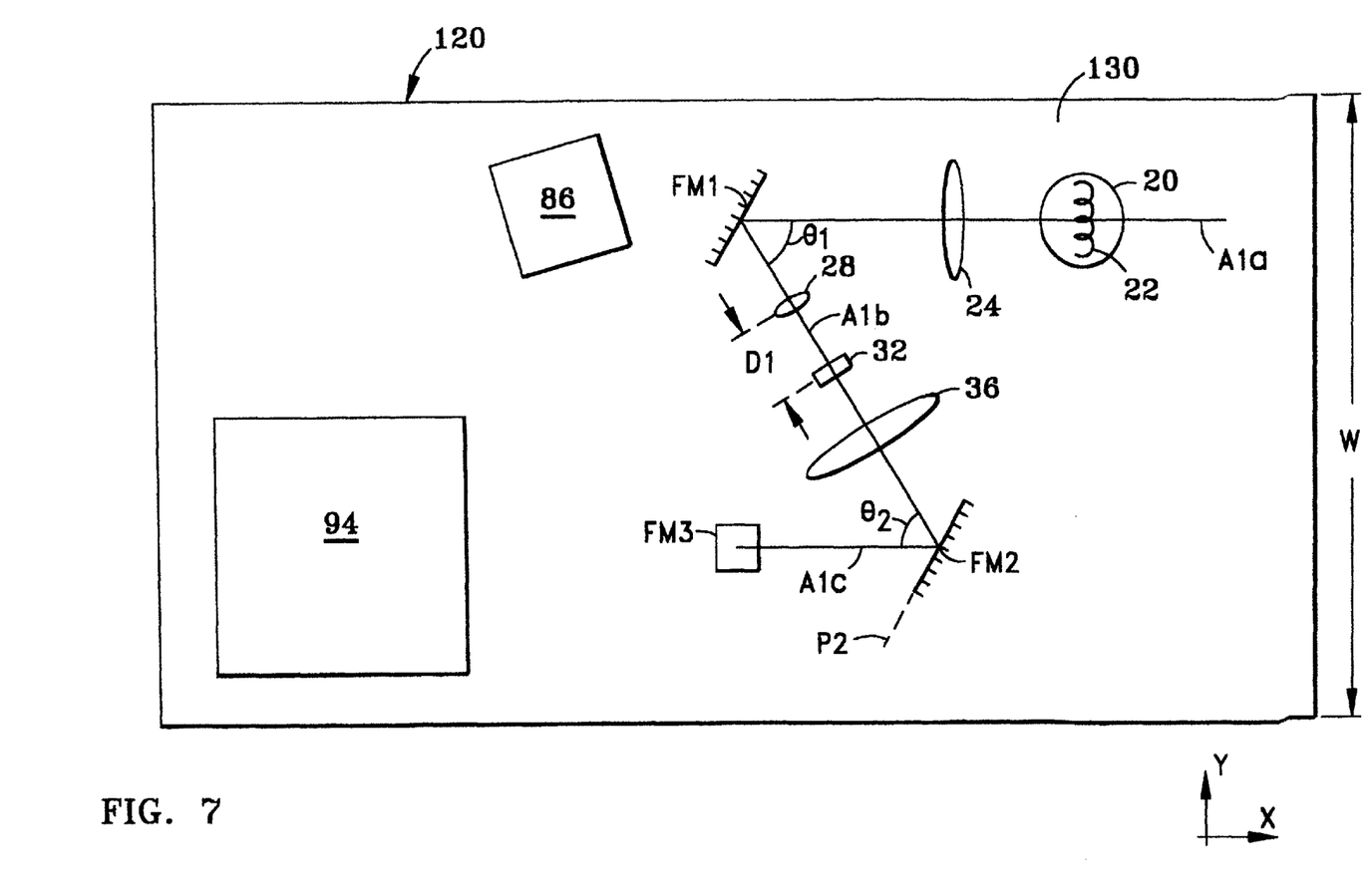
FIG. 7 is a top view of the upper plane of the folded schematic reflectometer system of the present invention as contained with the housing and reflectometer volume shown in FIG. 5.

As mentioned above, the placement of fold mirrors FM1–FM6 in reflectometer 10 is very important in achieving a highly compact reflectometer system. With reference now to FIG. 6, the main optical paths in reflectometer 10 reside primarily within two substantially parallel planes, an upper plane 130 and a lower plane 134 separated by a distance ΔZ. Distance ΔZ is between about 1 cm and about 10 cm and is preferably about 2.5 cm. With reference also to FIG. 7, plane 130 (which is in the plane of the paper in FIG. 7) contains axes A1*a*, A1*b* and A1*c* along which the elements of illumination subsystem IS from light source 20 through fold mirror FM3 are disposed. Thus, most of illuminator subsystem IS is contained in upper plane 130. This is desirable because it allows light source 20 to be placed in an upper corner of housing 120 where it is easily accessible for replacement.

With reference to FIG. 7, fold mirrors FM1, FM2 and FM3 are shown disposed in fold mirror mounting planes P1, P2 and P3, respectively. Fold mirror FM1 creates axis A1*b* and redirects light beam Bi traveling along axis A1*a*, to travel along an axis A1*b*. Light source 20 and lens 24 are disposed along an axis A1*a*, and aperture stop 28, field stop 32, and lens 36 are disposed along axis A1b. Axes A1a and A1b form an angle θ1 at FM1 of between 0 and 90 degrees, and preferably is about 74 degrees.

Fold mirror FM1 cannot be placed before lens 24, due to the short distance between this lens and light source 20. Also, fold mirror FM1 cannot be placed after aperture stop 28 due to the short axial distance D1 between aperture stop 28 and field stop 32.

Fold mirror FM2 is located adjacent lens 36 and creates axis A1c and redirects light beam Bi transmitted through lens 36 and traveling along axis A1b to travel along an axis A1c.

Axes A1b and A1c form an angle θ2 at FM2 of between 0 and 90 degrees and is preferably about 74 degrees.

Fold mirrors FM1 and FM2 are arranged such that angles θ1 and θ2 minimize the width w of reflectometer 10. However, the reflectance of fold mirrors FM1 and FM2 is maximum (in the desired wavelength range) at an angle of incidence of about 45 degrees. Setting angles θ1 and θ2 to be about 74 degrees gives an angle of incidence of about 37 degrees, which does not significantly degrade performance, yet provides a compact width W for reflectometer 10.

Figure 8:
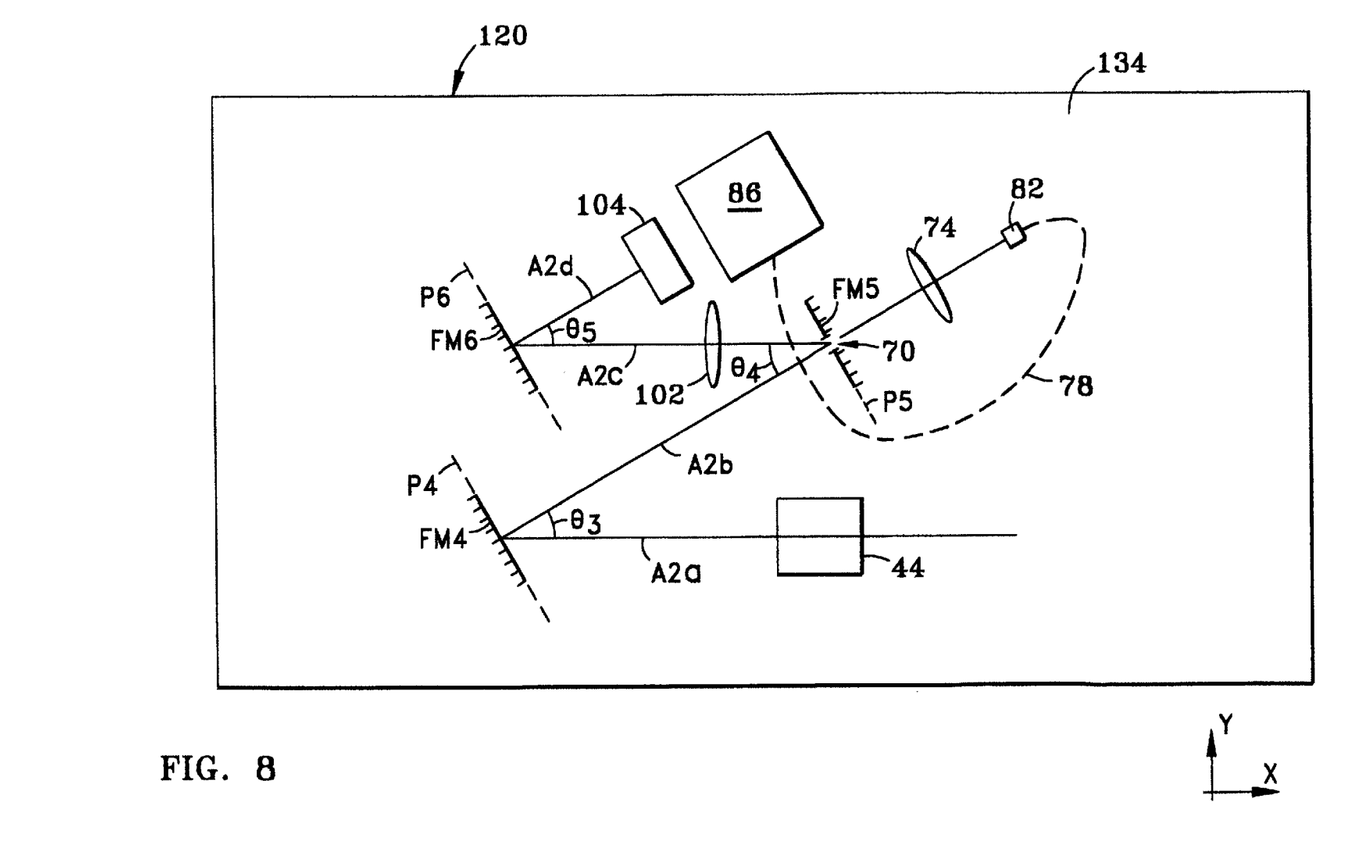
FIG. 8 is a top view of the lower plane of the folded schematic reflectometer system of the present invention as contained within the housing and reflectometer volume shown in FIG. 5.

With continuing reference to FIGS. 6–8, fold mirror FM3 is disposed along axis A1c and is tilted in the Z-direction at an angle of approximately 45 degrees with respect to the X-Y plane. Fold mirror FM3 creates axis A1d and redirects beam Bi transmitted through lens 36 to travel in substantially the negative Z direction along axis A1d to beam splitter 44, located at the intersection of axes A1d and A2a (see FIG. 6).

With reference now to FIGS. 6 and 8, lower plane 134 included axes A2a–A2d. Fold mirror FM4 is disposed in plane P4 and creates axis A2b. Fold mirror FM4 and redirects light beams Br and Bi traveling away from beam splitter 44 along axis A2a to travel along axis A2b to fold mirror FM5 disposed in plane P5. Axes A2a and A2b form an angle θ3 between 0 and 90 degrees and preferably about 17 degrees. Further, fold mirror FM5 creates axis A2c and forms light beam Bv which travels along axis A2c. Axes A2b and A2c form an angle θ4 of between 0 and 90 degrees and preferably about 19 degrees.

Also, fold mirror FM6 disposed in plane P6 creates axis A2d and redirects light beam Bv to travel along axis A2d to video camera 104. Axes A2c and A2d form an angle θ5 of between 0 and 90 degrees and preferably about 26 degrees.

The positions of fold mirrors FM4, FM5 and FM6 and angles θ3, θ4, and θ5 associated with the respective axes intersecting these fold mirrors are all chosen to minimize the size of reflectometer 10 of the present invention, while at the same time not allowing the light beam to be vignetted by an adjacent component. For example, if angle θ4 is reduced, then lens 102 will vignette sample light beam Bs as it travels along axis A2b. If angle θ5 is reduced, then lens 102 and video camera 104 will vignette light beam Bv as it travels along axes A2b and A2c.

The mechanical construction of reflectometer 10 of the present invention is an important in meeting the performance and compactness goals of the present invention. In a preferred embodiment, reflectometer 10 includes three machined plates comprised of aluminum. These plates are bolted together to form a single, core modular integrated structure. Since all the optical components in reflectometer 10 are mounted to this core structure, temperature changes have very little effect on the alignment of the reflectometer, since the components expand and contract together. This creates a reflectometer 10 which is extremely robust and stable over time, a feature which is highly valued in the semiconductor arts. Furthermore, because the optical path is nearly completely enclosed by housing 120 (except for a small portion of lens 52 extending from the housing by a distance ΔH), reflectometer 10 is substantially immune to temperature changes and airflow through the environment. These advantages are, in large measure, a result of achieving such a highly compact design.

Working Example

Figure 9:
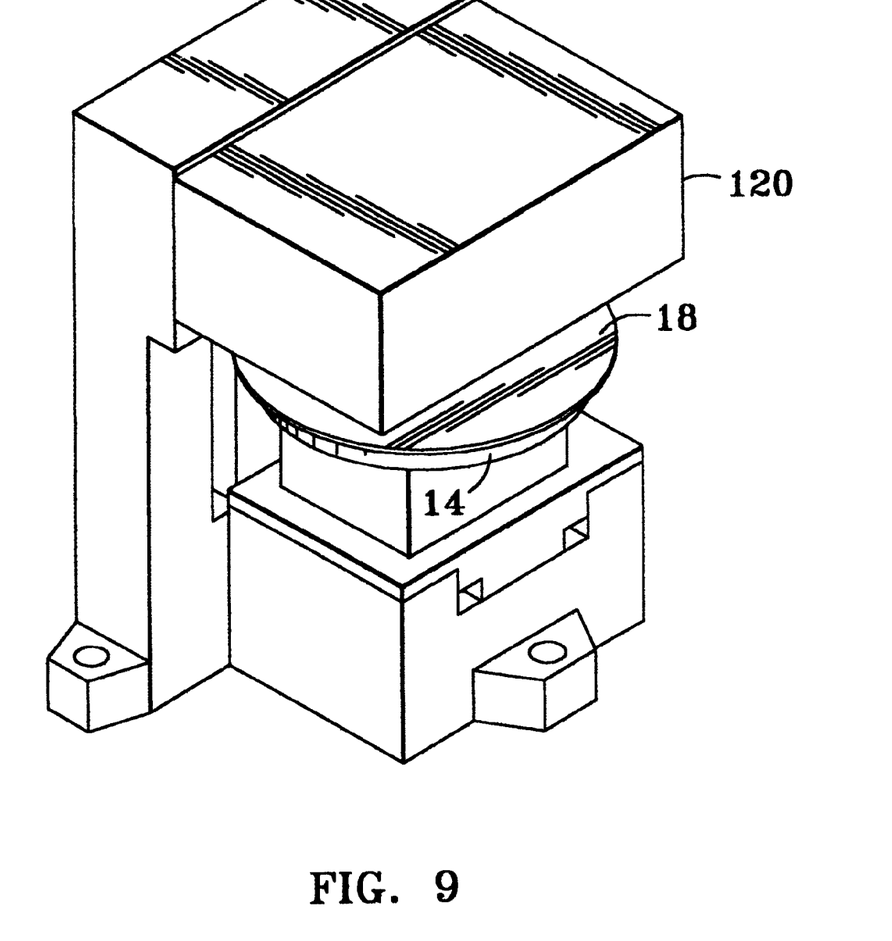
FIG. 9 is an isometric view of an integrated metrology system which includes the reflectometer system of the present invention.
Figure 10:
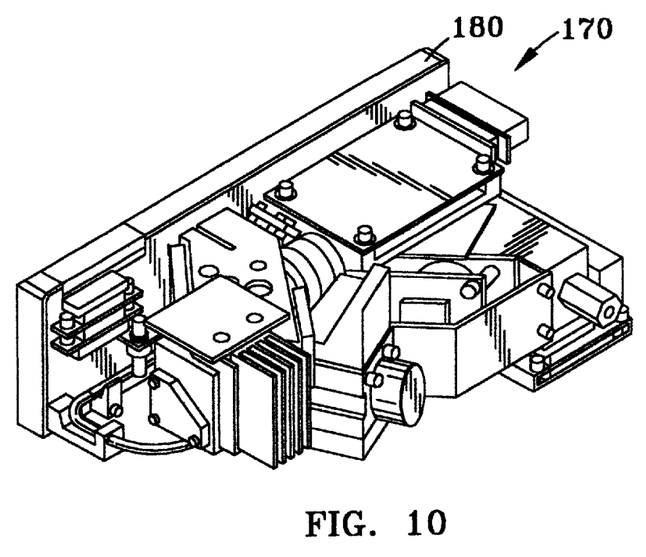
FIG. 10 is a perspective view of a Working Example of the reflectometer system of the present invention.
Figure 11:
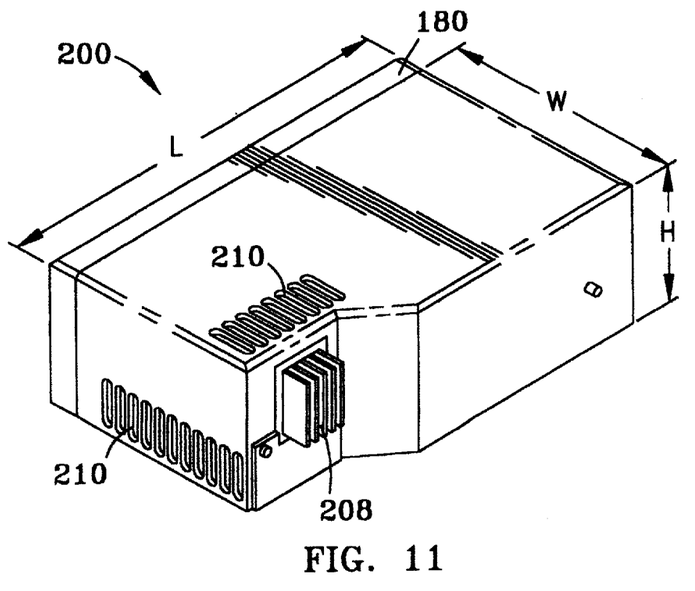
FIG. 11 is a perspective view of a reflectometer housing, similar to that shown in FIG. 5, suitable for use with the Working Example of the present invention as shown in FIG. 10.

Below are Tables 1–3 setting forth design values for a Working Example of the reflectometer of the present invention. FIG. 9 is an isometric view of an integrated metrology system, which includes reflectometer system 10 of the present invention enclosed in housing 120 (see FIG. 5). The dimensions of the metrology system are 28 cm ×28 cm×25 cm, which translates into a volume of 0.7 square meters. This is in contrast to prior art systems, which typically occupy 1.4 to 2 square meters. The reflectometer of the present invention allows for an increase in compactness in metrology tools by a factor of about 20. FIG. 10 is a perspective view of reflectometer 170 of Working Example 1, and includes all the elements described above in connection with reflectometer 10 and FIGS. 1–3. Also shown is a back plate 180 for supporting reflectometer 170. FIG. 11 illustrates a housing 200 which is similar to housing 120 of FIG. 5, and is suitable for use with reflectometer 170 and has similar dimensions. Housing 200 is discussed in further detail below.

In Tables 1–3 below, S is the surface of the element described, r is the radius of curvature, d is the axial separation between surfaces, "medium" is the medium (e.g., glass or air), and "diameter" is the diameter (i.e., clear aperture) of the particular element.

TABLE 1

ILLUMINATION SUBSYSTEM (IS) PATH

| S | R | d | medium | diameter |
|---|---|---|---|---|
| light source 20 | | 19.995 | air | 2 |
| lens 24 | Infinity | 5.5 | B270 | 15 |
| lens 24 | Asphere | 12.605 | air | 15 |
| fold mirror FM1 | Infinity | 7.3 | mirror | |
| aperture stop 28 | Infinity | 22.63 | air | 2 |
| field stop 32 | Infinity | 12.74 | air | |
| lens 36 | 41.399 | 2 | SF2 | 15 |
| lens 36 | 13.39 | 6 | BK7 | 15 |
| lens 36 | −18.1699 | 10.29 | air | 15 |
| fold mirror FM2 | Infinity | 19.05 | mirror | 12.7 |
| shutter 40 | | 42.5196 | aluminum | |
| fold mirror FM3 | Infinity | 25.3852 | mirror | 12.7 |
| beamsplitter 44 | Infinity | 12.7 | BK7 with coating | 12.7 |
| beamsplitter 44 | Infinity | 11.257 | air | 12.7 |
| aperture stop 48 | | 2.522 | air | |
| lens 52 | −17.691 | 6.169 | BK7 | |
| lens 52 | 11.781 | 2.057 | SF2 | |
| lens 52 | 42.891 | 33.628 | air | |
| sample 18 | infinity | | | |

Total Path Length for Illumination subsystem IS: 254.35 mm

TABLE 2

SIGNAL SUBSYSTEM (SS) PATH

| S | r | d | medium | diameter |
|---|---|---|---|---|
| sample 18 | | 33.628 | | |
| lens 52 | 42.891 | 2.057 | SF2 | 15 |
| lens 52 | 11.781 | 6.169 | BK7 | 15 |
| lens 52 | −17.691 | 2.522 | air | 15 |
| aperture stop 48 | | 14 | air | |

TABLE 2-continued

SIGNAL SUBSYSTEM (SS) PATH

| S | r | d | medium | diameter |
|---|---|---|---|---|
| beamsplitter 44 | infinity | 12.7 | BK7 with coating | 12.7 |
| beamsplitter 44 | infinity | 59.817 | air | 12.7 |
| fold mirror FM4 | infinity | 76.556 | mirror | 12.7 |
| fold mirror FM5 | infinity | 7.21 | air | |
| lens 74 | 6.23 | 2.5 | BK7 | 6 |
| lens 74 | 6.23 | 28.45 | air | 6 |
| fiber optic 78 | infinity | 240 | | 0.5 |
| spectrometer 86 | | | | |

Total Path Length for Signal Subsystem SS: 245.61 mm (w/fiber optic = 485.61 mm)

TABLE 3

VIEWING SUBSYSTEM (VS) PATH

| S | r | d | medium | diameter |
|---|---|---|---|---|
| sample 18 | | 33.628 | | |
| lens 52 | 42.891 | 2.057 | SF2 | 15 |
| lens 52 | 11.781 | 6.169 | BK7 | 15 |
| lens 52 | −17.691 | 2.522 | | 15 |
| aperture stop 48 | | 14 | | |
| beamsplitter 44 | infinity | 12.7 | | 12.7 |
| beamsplitter 44 | infinity | 59.817 | | 12.7 |
| fold mirror FM4 | infinity | 76.556 | mirror | 12.7 |
| fold mirror FM5 | infinity | 64.622 | mirror | |
| lens 110 | 23.3951 | 4.9 | BK7 | 15 |
| lens 110 | −17.6 | 2 | SF2 | 15 |
| lens 110 | −60.31 | 37.341 | | 15 |
| fold mirror FM6 | infinity | 58.7756 | | 12.7 |
| video camera 104 | infinity | | | |

Total Path Length for Viewing Subsystem VS: 375.088 mm

From Tables 1 and 3, the combined optical path length of illumination subsystem IS and signal subsystem SS, without accounting for fiber optic 78, is about 500 mm. The combined optical path length of illumination subsystem IS and signal subsystem SS, including fiber optic 78, is about 720.3 mm. From Tables 1–3, the total of the optical paths for the subsystems of reflectometer 10, excluding fiber optic 78, is about 0.9 meters.

In the Working Example, reflectometer 170 is substantially enclosed by housing 200 similar to housing 120 (FIG. 5), which is attached to back plate 180. Housing 200 includes a heat sink 208 for dissipating heat from the light source, and vents 210 for venting heat from inside the housing. Housing 200 has dimensions L×W×H of approximately 25.4 cm×12.5 cm×10 cm, with ΔH=3 mm (not shown in FIG. 11; see FIG. 5). Thus, housing 200 encloses a housing volume V of about 0.0032 cubic meters, with an associated reflectometer volume V' which is larger than V by only 1.5 cubic centimeters.

While the present invention has been described in connection with preferred embodiments and a Working Example, it will be understood that it is not limited to those embodiments and the Working Example. On the contrary, it is intended to cover all alternatives, modifications and equivalents as may be included within the spirit and scope of the invention as defined in the appended claims.

What is claimed is:

1. A compact reflectometer system capable of measuring reflectance from a sample, comprising:
   a) an illumination system for illuminating the sample, said illumination subsystem having a light source, and at least one illumination subsystem fold mirror;
   b) a signal subsystem for measuring at least one wavelength of light from said light source reflected from the sample, said signal subsystem including at least one signal subsystem fold mirror;
   c) a viewing subsystem for viewing the sample, said viewing subsystem including at least one viewing subsystem fold mirror; and
   d) wherein said illuminating, signal and viewing subsystems occupy a volume of less than or equal to approximately 0.006 cubic meters.

2. A compact reflectometer according to claim 1, wherein:
   a) a portion of said illumination subsystem is arranged in a first plane; and
   b) said signal, and viewing subsystems are arranged in a second plane substantially parallel to said first plane.

3. A compact reflectometer according to claim 2, wherein said first and second planes are separated by a distance ΔZ, wherein 1 cm≦ΔZ≦10 cm.

4. A compact reflectometer according to claim 2, wherein said at least one fold mirror directs a light beam traveling in said illumination subsystem substantially parallel in said first plane, toward said second plane.

5. A compact reflectometer according to claim 2, wherein:
   a) said illumination subsystem includes first and second illumination subsystem fold mirrors, said signal subsystem includes a first signal subsystem fold mirror, and said viewing subsystem includes first and second viewing subsytem fold mirrors;
   b) said first plane includes first, second and third axes, wherein said first and second axes intersect at said first subsystem fold mirror at an angle θ1, and wherein said second and third axes intersect at said second illumination subsystem fold mirror at an angle θ2; and
   c) said second plane includes fourth, fifth, sixth and seventh axes, wherein said fourth and fifth axes intersect at said first signal subsystem fold mirror at an angle θ4, said fifth and sixth axes intersect said first viewing subsystem fold mirror at an angle θ5, and said sixth and seventh axes intersect said second viewing subsystem fold mirror at an angle θ6.

6. A compact reflectometer according to claim 5, wherein θ1 is approximately 74 degrees, θ2 is approximately 74 degrees, θ3 is approximately 17 degrees, θ4 is approximately 19 degrees, and θ5 is approximately 26 degrees.

7. A compact reflectometer according to claim 2, wherein said first plane includes at least three fold mirrors and said second plane includes at least three fold mirrors.

8. A compact reflectometer system according to claim 1, wherein:
   a) said illumination subsystem further includes, sequentially toward the sample, said light source, a first lens, a first illumination subsystem fold mirror, a first aperture stop, a field stop, a second lens, a second illumination subsystem fold mirror, a first shutter, a third illumination subsystem fold mirror, a beam splitter, a second aperture stop, and a third lens, wherein said first illumination subsystem fold mirror is disposed between said first lens and said first aperture stop, said second illumination subsystem fold mirror is disposed between said second lens and said first shutter, and said third illumination subsystem fold mirror is disposed between said first shutter and said beam splitter;
   b) said signal subsystem further includes, sequentially from the sample, said third lens, said second aperture stop, said beam splitter, said fourth lens said fiber optic, and a spectrometer; and
   c) said viewing subsystem further includes, sequentially from the sample, said third lens, said second aperture stop, said beam splitter, a first viewing subsystem fold mirror, a fifth lens, a second viewing subsystem fold mirror and a video camera, wherein said first viewing subsystem fold mirror is disposed between said beam splitter and said fourth lens, and said second viewing subsystem fold mirror is disposed between said fifth lens and said video camera.

9. A compact reflectometer according to claim 8, further including:

a) a spectrometer electronics unit connected to said spectrometer; and b) a computer connected to said spectrometer electronics and said video camera.

10. A compact reflectometer system capable of measuring reflectance from a sample, comprising:

a) a light source for emitting a light beam;

b) an illumination subsystem designed to focus said beam to form a measurement spot on the sample;

c) a signal subsystem for detecting said beam after it has reflected from the sample;

d) a viewing subsystem for viewing a field of view surrounding said measurement spot, said viewing system having a distortion of less than 2% at 1.3 mm of said field of view; and e) a plurality of fold mirrors disposed such that the reflectometer occupies a volume of less than or equal to approximately 0.006 cubic meters.

11. A compact reflectometer system according to claim 10, further including a housing having a housing volume substantially equal to said reflectometer volume.

12. A compact reflectometer system comprising:

a) an illumination subsystem having a first optical path;

b) a signal subsystem having a second optical path; and c) wherein said first and second optical paths have a combined length of at least 480 mm and the reflectometer occupies a volume less than or equal to about 0.006 cubic meters.

13. A compact reflectometer system comprising:

a) an illumination subsystem having a first optical path;

b) a signal subsystem having a second optical path;

c) a viewing subsystem having a third optical path; and d) wherein said first, second and third optical paths have a combined length of approximately 0.875 meters and the reflectometer occupies a volume of no more than about 0.006 cubic meters.

14. A compact reflectometer system according to claim 13, wherein said signal subsystem includes a fiber optic having an fourth optical path.

15. A compact reflectometer system according to claim 13, wherein the system includes at least six fold mirrors.

16. A compact reflectometer according to claim 15, wherein three fold mirrors are arranged in a first plane and three fold mirrors are arranged in a second plane parallel to said first plane.

17. A compact reflectometer system according to claim 13, further including a housing having a housing volume substantially the same as said reflectometer volume.

18. A compact reflectometer system having the properties and characteristics as set forth in the Tables 1–3:

TABLE 1

ILLUMINATION SUBSYSTEM (IS) PATH

| S | R | d | medium | diameter |
| --- | --- | --- | --- | --- |
| light source 20 | | 19.995 | air | 2 |
| lens 24 | Infinity | 5.5 | B270 | 15 |
| lens 24 | Asphere | 12.605 | air | 15 |
| fold mirror FM1 | Infinity | 7.3 | mirror | |
| aperture stop 28 | Infinity | 22.63 | air | 2 |
| field stop 32 | Infinity | 12.74 | air | |
| lens 36 | 41.399 | 2 | SF2 | 15 |
| lens 36 | 13.39 | 6 | BK7 | 15 |
| lens 36 | −18.1699 | 10.29 | air | 15 |
| fold mirror FM2 | Infinity | 19.05 | mirror | 12.7 |
| shutter 40 | | 42.5196 | aluminum | |
| fold mirror FM3 | Infinity | 25.3852 | mirror | 12.7 |
| beamsplitter 44 | Infinity | 12.7 | BK7 with coating | 12.7 |
| beamsplitter 44 | Infinity | 11.257 | air | 12.7 |
| aperture stop 48 | | 2.522 | air | |
| lens 52 | −17.691 | 6.169 | BK7 | |
| lens 52 | 11.781 | 2.057 | SF2 | |
| lens 52 | 42.891 | 33.628 | air | |
| sample 18 | infinity | | | |

Total Path Length for Illumination subsystem IS: 254.35 mm

TABLE 2

SIGNAL SUBSYSTEM (SS) PATH

| S | r | d | medium | diameter |
| --- | --- | --- | --- | --- |
| sample 18 | | 33.628 | | |
| lens 52 | 42.891 | 2.057 | SF2 | 15 |
| lens 52 | 11.781 | 6.169 | BK7 | 15 |
| lens 52 | −17.691 | 2.522 | air | 15 |
| aperture stop 48 | | 14 | air | |
| beamsplitter 44 | infinity | 12.7 | BK7 with coating | 12.7 |
| beamsplitter 44 | infinity | 59.817 | air | 12.7 |
| fold mirror FM4 | infinity | 76.556 | mirror | 12.7 |
| fold mirror FM5 | infinity | 7.21 | air | |
| lens 74 | 6.23 | 2.5 | BK7 | 6 |
| lens 74 | 6.23 | 28.45 | air | 6 |
| fiber optic 78 | infinity | 240 | | 0.5 |
| spectrometer 86 | | | | |

Total Path Length for Signal Subsystem SS: 245.61 mm (w/fiber optic = 485.61 mm)

TABLE 3

VIEWING SUBSYSTEM (VS) PATH

| S | r | d | medium | diameter |
| --- | --- | --- | --- | --- |
| sample 18 | | 33.628 | | |
| lens 52 | 42.891 | 2.057 | SF2 | 15 |
| lens 52 | 11.781 | 6.169 | BK7 | 15 |
| lens 52 | −17.691 | 2.522 | | 15 |
| aperture stop 48 | | 14 | | |
| beamsplitter 44 | infinity | 12.7 | | 12.7 |
| beamsplitter 44 | infinity | 59.817 | | 12.7 |
| fold mirror FM4 | infinity | 76.556 | mirror | 12.7 |
| fold mirror FM5 | infinity | 64.622 | mirror | |
| lens 110 | 23.3951 | 4.9 | BK7 | 15 |
| lens 110 | −17.6 | 2 | SF2 | 15 |
| lens 110 | −60.31 | 37.341 | | 15 |
| fold mirror FM6 | infinity | 58.7756 | | 12.7 |
| video camera 104 | infinity | | | |

Total Path Length for Viewing Subsystem VS: 375.088 mm.

\* \* \* \* \*

UNITED STATES PATENT AND TRADEMARK OFFICE
CERTIFICATE OF CORRECTION

PATENT NO. : 6,181,427 B1
DATED : January 30, 2001
INVENTOR(S) : Richard A. Yarussi and Blaine R. Spady It is certified that error appears in the above-identified patent and that said Letters Patent is hereby corrected as shown below:

Column 12,
Line 64, after the word "lens" insert a -- , --.

Column 13,
Line 55, delete the word "an" and substitute therefor -- a --.

Signed and Sealed this

Seventh Day of May, 2002

*Attest:*

*Attesting Officer*

JAMES E. ROGAN
*Director of the United States Patent and Trademark Office*